(12) United States Patent
Tamir-Kheli et al.

(10) Patent No.: US 7,943,401 B2
(45) Date of Patent: May 17, 2011

(54) DETECTION AND REDUCTION OF DIELECTRIC BREAKDOWN IN SEMICONDUCTOR DEVICES

(75) Inventors: Jamil Tamir-Kheli, Los Angeles, CA (US); William A. Goddard, III, Pasadena, CA (US); Masayasu Miyata, Nagano-ken (JP)

(73) Assignee: California Institute of Technology, Pasadena, CA (US)

( * ) Notice: Subject to any disclaimer, the term of this patent is extended or adjusted under 35 U.S.C. 154(b) by 242 days.

(21) Appl. No.: 12/114,587

(22) Filed: May 2, 2008

(65) Prior Publication Data

US 2008/0211500 A1    Sep. 4, 2008

Related U.S. Application Data

(63) Continuation of application No. 10/950,287, filed on Sep. 24, 2004, now abandoned.

(51) Int. Cl.
*H01L 21/66* (2006.01)
(52) U.S. Cl. .............. 438/17; 438/10; 438/14; 438/18
(58) Field of Classification Search ............. 438/10, 438/14, 17–18
See application file for complete search history.

(56) References Cited

U.S. PATENT DOCUMENTS

| | | | | |
|---|---|---|---|---|
| 4,668,653 | A * | 5/1987 | Teller et al. | 502/215 |
| 5,198,392 | A * | 3/1993 | Fukuda et al. | 438/769 |
| 5,885,666 | A * | 3/1999 | Doll et al. | 427/530 |
| 6,214,561 | B1 * | 4/2001 | Peters et al. | 435/7.1 |
| 6,633,392 | B1 * | 10/2003 | Singh et al. | 356/630 |
| 2005/0037615 | A1 * | 2/2005 | Cabib et al. | 438/689 |
| 2006/0084236 | A1 * | 4/2006 | Vogt | 438/381 |

OTHER PUBLICATIONS

Wikipedia, Stark effect; "http://en.wikipedia.org/wiki/Stark_effect".*
Encyclopedia Britannica, Stark effect.*
Wikipedia, Zeeman effect; "http://en.wikipedia.org/wiki/Zeeman_effect".*
Encyclopedia Britannica, Zeeman effect.*

* cited by examiner

*Primary Examiner* — Kevin M Picardat
*Assistant Examiner* — Bac H Au
(74) *Attorney, Agent, or Firm* — Loeb & Loeb LLP

(57) ABSTRACT

Methods for detecting the breakdown potential of a semiconductor device having a thin dielectric layer are disclosed. The method includes measuring a spectroscopy of the thin dielectric layer and determining whether the spectroscopy exhibits the presence of a breakdown precursor ($H_2$, H interstitial radical, H attached radical, and H attached dimer). Preferably, the method is carried out in the presence of a substantially significant applied electric field across dielectric layer. A semiconductor device tested in accordance with this method is also disclosed. Additionally, methods for reducing dielectric breakdown of a semiconductor device having a thin dielectric layer involving the substitution of a second molecule for $H_2$ molecules present in the dielectric. This second molecule preferably does not react with Si or O to form an undesired attached state and may be an inert gas having a molecular size approximating that of a Hydrogen atom, such as Helium. A semiconductor device made using this method is also disclosed.

25 Claims, 6 Drawing Sheets

DETECTION AND REDUCTION OF DIELECTRIC BREAKDOWN IN SEMICONDUCTOR DEVICES

CROSS-REFERENCE TO RELATED APPLICATION

This application claims benefit under 35 U.S.C. §119(e) to provisional patent application Ser. No. 60/506,453 filed on Sep. 26, 2003 entitled "Mechanism of Dielectric Breakdown."

BACKGROUND OF THE INVENTION

1. Field of the Invention

The present invention is directed to methods for improving semiconductor devices and, in particular, to methods and apparatuses for the detection and reduction of dielectric breakdown in such devices.

2. Background Art

In general, the gate oxide thickness for the current generation of field-effect transistors (FET) is approximately 50 Angstroms. The next generation of FETs will require thinner oxides in order to achieve desired miniaturization. However, with current technology the electron current that would leak through a thinner gate oxide during transistor usage would be too large to prove useful. In fact, such large leakage currents would likely lead to permanent damage of the oxide layer, potentially damaging the FET in minutes. These leakage currents are thought to be due to dielectric breakdown in the insulating layers. This makes dielectric breakdown a critical issue in the miniaturization of FETs and other semiconductor devices. Yet, little, if anything, is understood about the mechanism responsible for dielectric breakdown in thin dielectric layers in electronic devices.

It is known the operating electric field increases as the dielectric thickness decreases. The electric field is the ratio of the applied voltage across the dielectric and its thickness. If the thickness is reduced by a factor of 2, then one could maintain exactly the same electric field by reducing the applied voltage by the same factor of 2. Unfortunately, one cannot scale the gate voltage down proportionally to the thickness because the voltage becomes too small to control the current across the FET between the source and drain. Thus, thinner dielectrics must operate with higher electric fields.

SUMMARY OF THE DISCLOSURE

The present disclosure uses quantum mechanics and molecular dynamics studies to derive a mechanism for breakdown in thin dielectrics. In particular, the present disclosure uses the case of silicon dioxide ($SiO_2$) gate materials in field-effect transistors (FET) to illustrate that the significantly larger electric fields associated with thin dielectrics cause H ("hydrogen interstitial radical") that can arise from $H_2$ ("hydrogen dimer") to react with defects and irregularities that occur inside the thin dielectric (insulator) and at its interface with the semiconductor ("insulator-semiconductor interface").

Hydrogen dimer ($H_2$) is a bound complex of two hydrogen atoms and is known to be ubiquitous inside current dielectrics. $H_2$ was never considered to be the source of dielectric breakdown. However, the present disclosure shows the surprising result that the reaction of $H_2$ with the defects and irregularities in the semiconductor device causes situations that can lead to increased leakage current and breakdown.

The present disclosure also teaches methods for reducing or eliminating the breakdown problem. In one aspect of the invention, the $H_2$ is pumped off and replaced with helium (He), for example. In addition, the present disclosure also teaches methods for detecting the potential failure by in situ or ex situ monitoring of spectroscopic and other characteristics of the sites causing breakdown, their precursors, and the presence of the $H_2$ and He.

BEST MODES OF CARRYING OUT THE INVENTION

The present disclosure teaches various methods for detecting the breakdown potential of a semiconductor device having a thin dielectric layer and methods for reducing that dielectric breakdown potential. Although the present specification is described in terms of $SiO_2$ field-effect transistors (FET), those working in the semiconductor processing industry generally understand that $SiO_2$ reacts much the same way as other semiconductor materials.

The semiconductor industry, as a whole, is generally trying to decrease oxide thicknesses to achieve increased device miniaturization. The existence of $H_2$ in dielectrics is widely known to be caused by all semiconductor processing methods. However, prior to the present invention, the existence of $H_2$ in dielectric materials was believed by the industry to be benign.

In semiconductor devices, as the dielectric (oxide) thickness is reduced, the size of the electric field inside the gate increases significantly. As a result of this significantly increased electric field, technologically relevant applied electric fields (about 10 million volts per centimeter or 10 MV/cm) lead to new chemical reactions not experienced previously. Some combination of this increased electric field and these resulting chemical reactions create novel electronic states in the dielectric that strongly increase the current flow of the dielectric and cause breakdown.

First, there is a particular state where a hydrogen atom "attaches" or weakly bonds to an oxygen atom in $SiO_2$ that can cause electron tunneling and breakdown. Based on quantum mechanical and force-field studies, this attached state was found to be 1.0 eV (electron volts) higher than the previously known interstitial hydrogen state in zero electric field. In an applied electric field, this attached state can become more stable than the interstitial state. In addition, two attached H states nearby can be further stabilized due to their large hybridization (attached dimer state).

Figure 1:
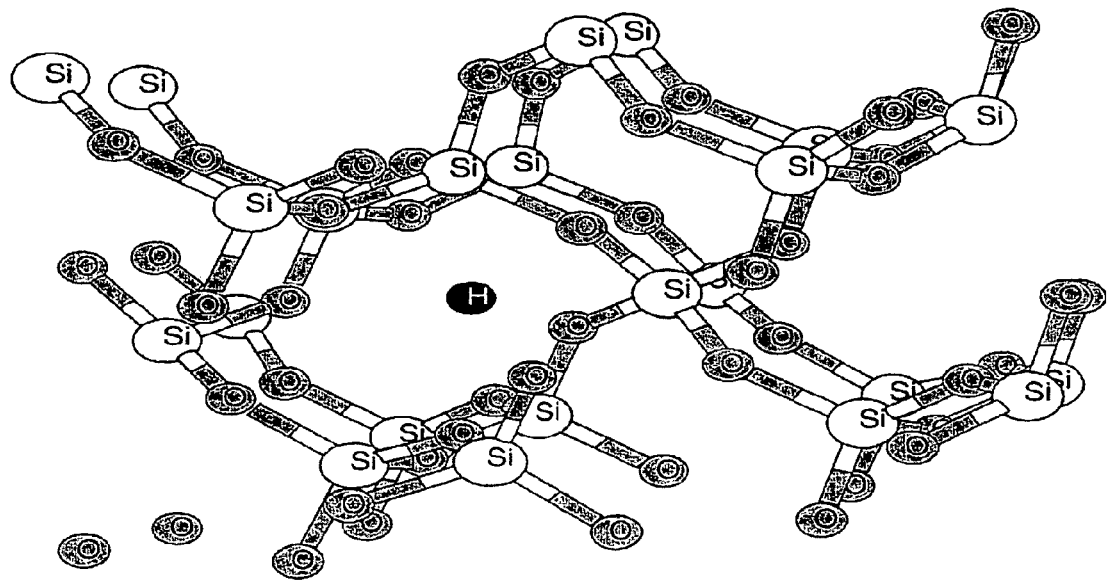
FIG. 1 of the drawings is a molecular model showing an H atom in an interstitial location ("H interstitial radical") in $SiO_2$.
Figure 2:
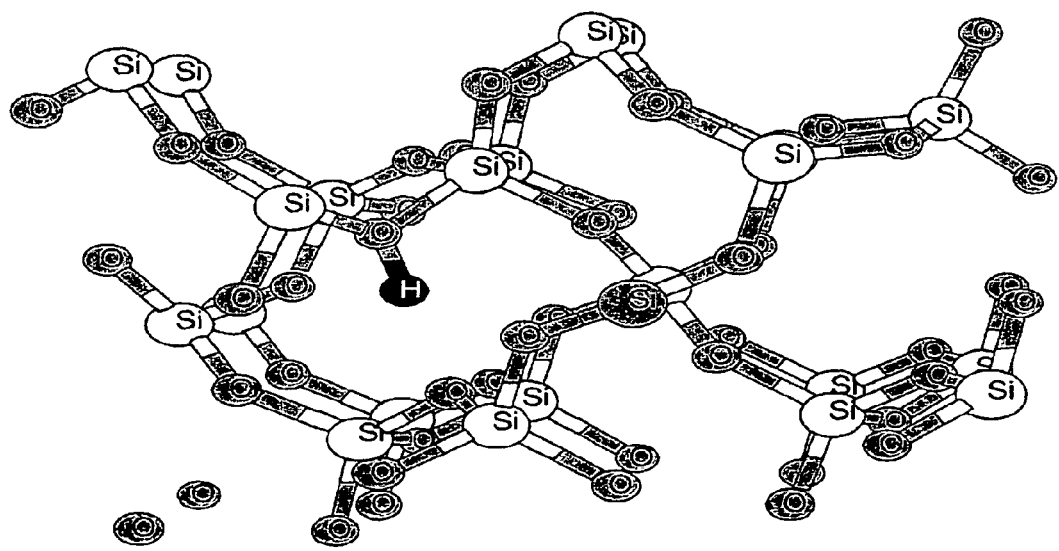
FIG. 2 of the drawings is molecular model showing an H atom attached ("attached radical") to an O atom that is part of the $SiO_2$ structure.

Second, there are two different chemical reactions that can create thermally accessible attached H dimer states under an applied electric field: (1) cracking $H_2$ in an interstitial region; and (2) cracking $H_2$ near a Silicon dangling bond (Pb center) near the Si—SiO2 interface, $H_2+Si$—$Si$—$H+$(attached H). FIG. 1 shows the well-characterized H atom in an interstitial location in a $SiO_2$ lattice. FIG. 2 shows a state with the H atom "attached" to an O atom that is 1.0 eV higher in energy. This state leads to an asymmetry in the Si—O bond lengths of the two Si bonded to the O attached to H. The O atom shifts 0.5 Angstroms towards H.

Figure 3:
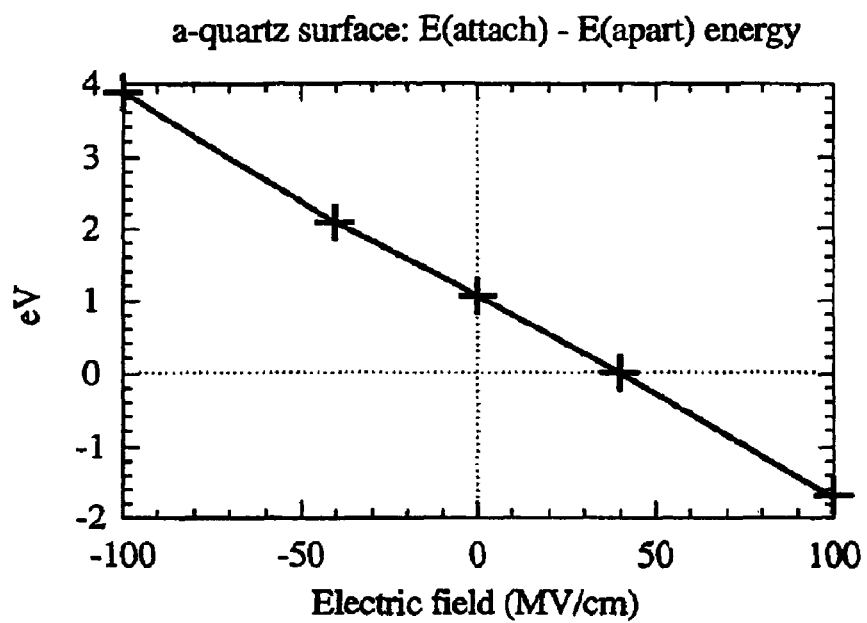
FIG. 3 of the drawings is a graph comparing the computed energies of an interstitial H in $SiO_2$ relative to an attached H in $SiO_2$ as a function of an external electric field.

FIG. 3 compares the energies of an interstitial H in $SiO_2$ relative to an attached H in $SiO_2$ as a function of an external electric field. These results are for a two dimensional $SiO_2$ slab terminated with H atoms. The field is applied in the upward direction in FIGS. 1 and 2. Since the dielectric constant of $SiO_2$ is approximately 4, the internal field is ¼ the external field value. Thus, for experimental fields from 10-20 MV/cm, or 40-80 MV/cm applied fields, the attached state is lower in energy than the apart state. Thus, the attached state becomes energetically favorable (more stable) for external fields larger than 40 MV/cm (million volts per centimeter).

Figure 4:
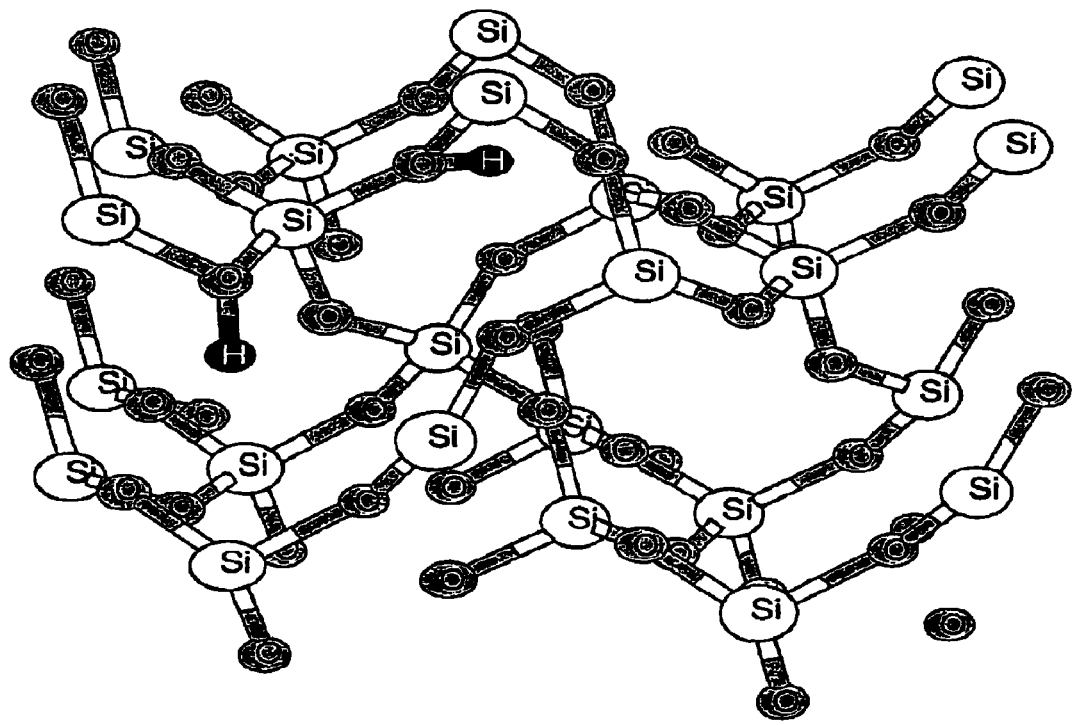
FIG. 4 of the drawings is a molecular model showing two H atoms attached at neighboring O sites ("attached dimer") in $SiO_2$.

In other words, as the foregoing describes, the strong electric field changes the chemistry of hydrogen bonding. The strong electric field makes a new quantum state accessible. The attached state has a large diffuse orbital with large amounts of charge on the nearby O and Si sites. This state will hybridize strongly with any other nearby attached state and lead to states in the $SiO_2$ bandgap with a large coupling to the metal electrodes generally found on each side of the gate oxide. The hybridization energy has been calculated to be 1.4 eV. This hybridized "attached dimer" state is shown in FIG. 4.

Figure 5:
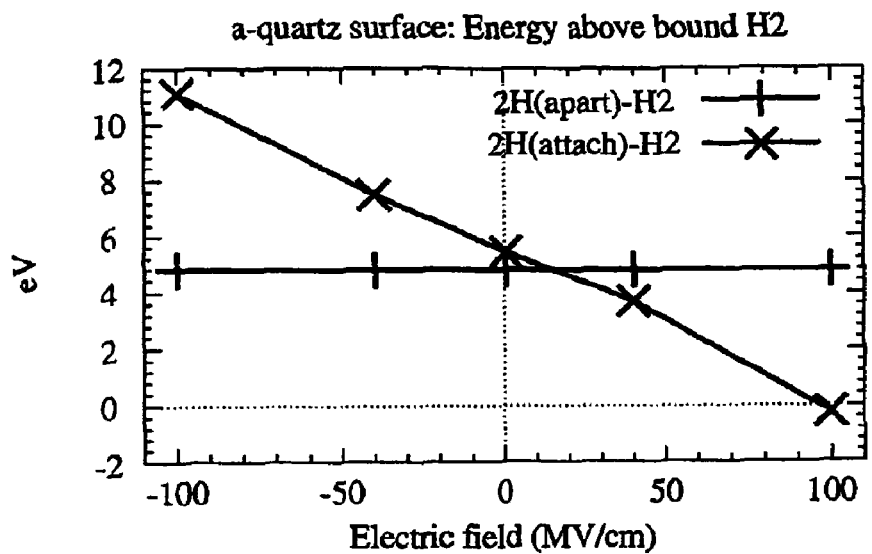
FIG. 5 of the drawings is a graph of two different computed relative energies: 1.) two H interstitial "apart" states minus $H_2$, and 2.) the attached dimer state minus $H_2$ dimer. Both lines are shown as a function of the external electric field.

FIG. 5 compares the relative energies of the attached dimer state to interstitial $H_2$ as a function of an external electric field. For sufficiently large electric fields, the attached dimer states becomes favorable. In particular, in the graphed example, the attached dimer state becomes energetically favorable (more stable) for external fields larger than 100 MV/cm. Using the dielectric constant of 4 as before, the experimental field is 25 MV/cm for the creation of the attached dimer.

The computed energies discussed above were calculated for the specific case of $SiO_2$ in a crystalline form (alpha quartz). In reality, $SiO_2$, like other dielectrics, is amorphous (irregular or disordered). This leads to strained Si—O bonds. The required electric fields for the creation of attached states will be reduced from the computed values for alpha-quartz for attachment to the strained bonds. Our estimates of the necessary electric fields for attached states are therefore higher (more conservative) than what is actually required.

Figure 6:
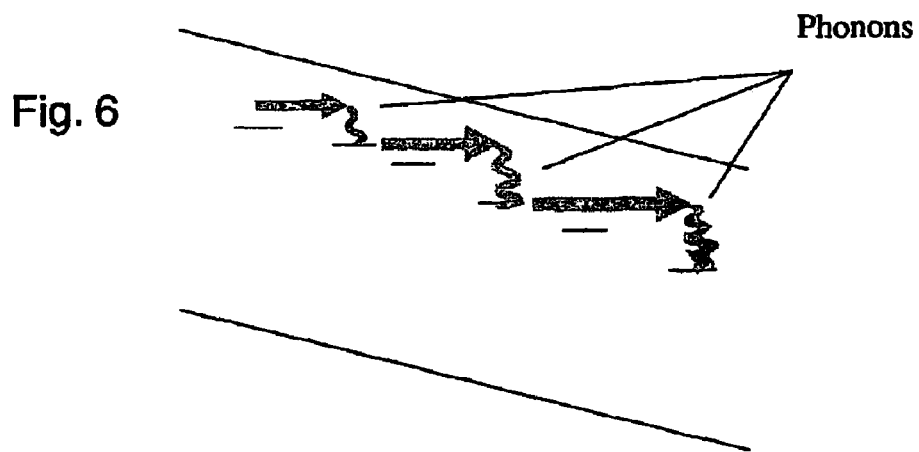
FIG. 6 of the drawings is a schematic representation of the energy loss to phonons from the acceleration of the electron through attached states.

Electron tunneling will occur between the attached dimers and these electrons can dissipate energy into the gate through phonons arising from the acceleration of the electron in the applied electric field. FIG. 6 shows a schematic of energy lost to phonons from acceleration of the electron through attached states.

The approximate observed reversibility of breakdown can be understood from electric field induced chemistry. For thicker dielectrics, the electric field is never large enough to make the attached state accessible and hence there is no breakdown For thinner dielectrics, however, the electric field is large enough to make the attached state chemistry accessible and easy electron tunneling can occur. This will over time lead to permanent damage to the dielectric structure due to the release of phonons in the gate by the mechanism shown in FIG. 6. If the field is turned off, then the attached states are lost and the system reverts back to its original state less whatever permanent damage occurred. Thus, one can understand the difference between soft and hard breakdown phenomena.

Figure 7:
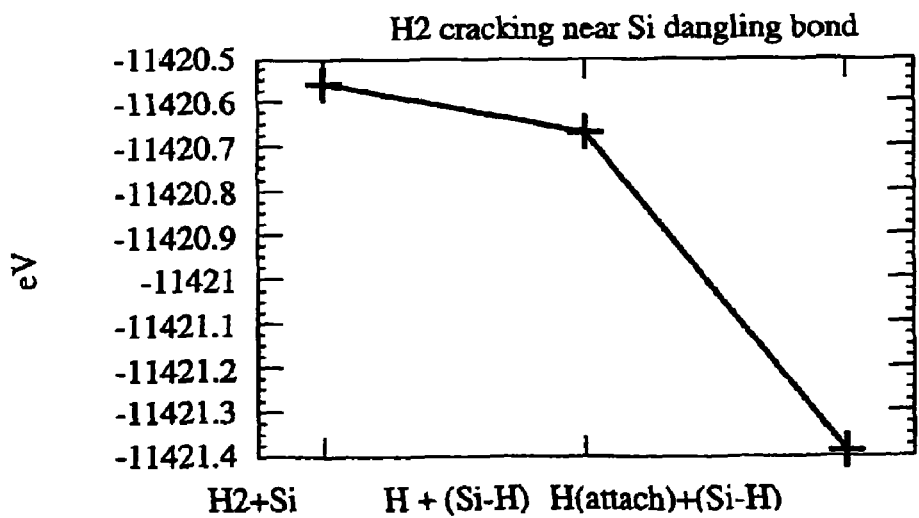
FIG. 7 of the drawings is a graphical representation of the computed energies for the creation of an attached H state in a zero electric field in the vicinity of a Si dangling bond.

FIG. 7 is another computed $H_2$ cracking pathway. FIG. 7 shows that $H_2$ cracking to passivate a Si dangling bond at the Si—$SiO_2$ interface along with the creation of an attached H state is energetically favorable even in zero electric field. Such Si dangling bonds are known to occur near the dielectric-semiconductor interface. This shows the formation of attached states occurs even without an electric field near the interface.

Based on this observed chemistry and novel electric field induced states, methods may be derived to detect and reduce this dielectric breakdown mechanism. In one embodiment, the detection of the potential or imminent failure may be performed by in situ or ex situ monitoring of spectroscopic and other characteristics of the sites causing breakdown, their precursors, and the presence of the $H_2$ and He.

Figure 8A:
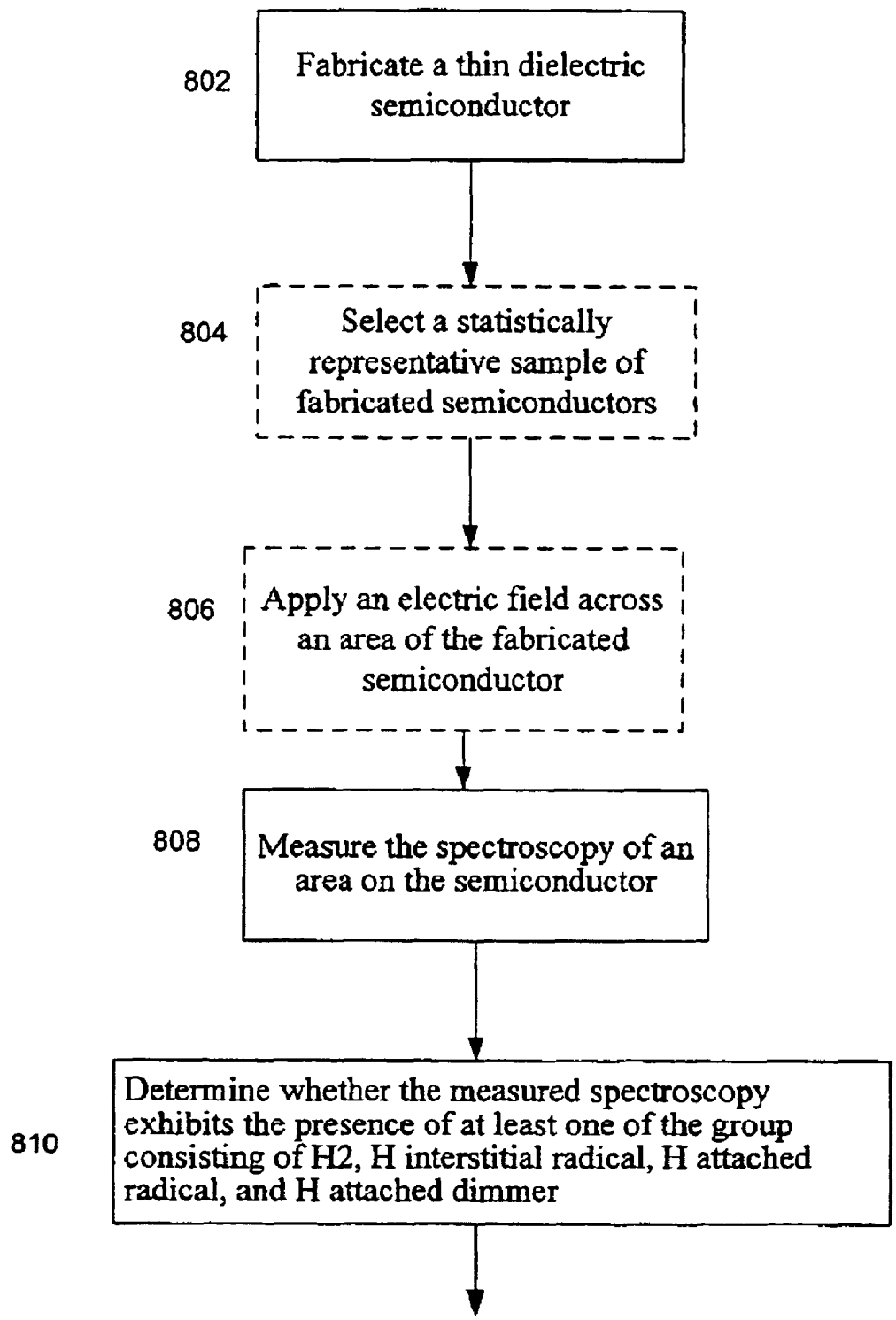
FIGS. 8a and 8b of the drawings are a flow diagram of a preferred approach for manufacturing a semiconductor device having a thin dielectric layer and detecting the breakdown potential thereof.
Figure 8B:
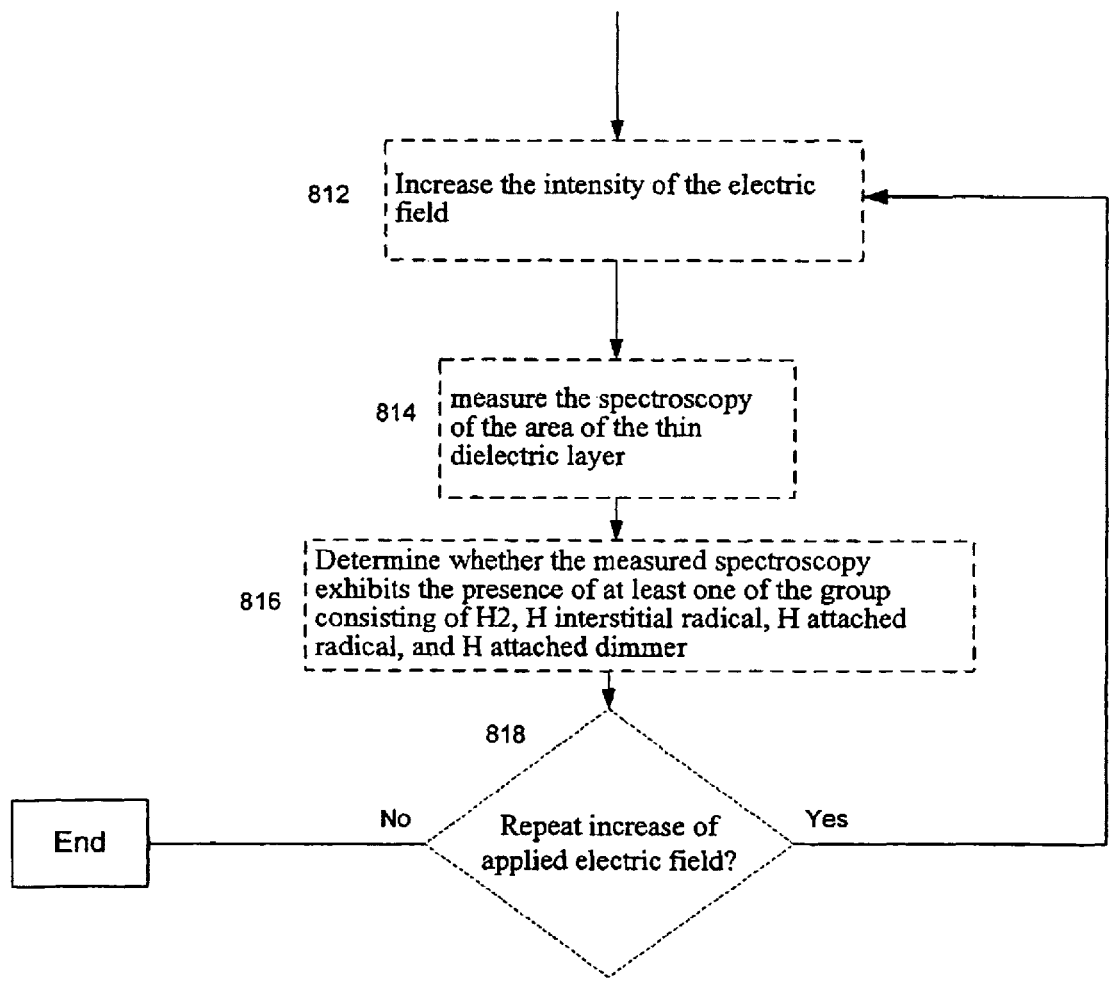

FIGS. 8*a* and 8*b* of the drawings are a flow diagram of a preferred approach to manufacturing a semiconductor device having a thin dielectric layer and detecting the breakdown potential thereof. In step 802, a semiconductor device, such as a FET, having a thin dielectric is fabricated. This fabrication may be any of the presently known techniques as well as presently unknown techniques that may be devised in the future. In one approach, a statistically representative sample of the semiconductor devices fabricated in a batch in step 802 are selected for testing, step 804. In another approach, all of the fabricated devices may be desired for testing, thus step 804 would be omitted in those instances.

In step 806, a substantially significant electric field may then be applied to a selected area of the thin dielectric layer of each individual semiconductor device selected for testing. In one embodiment, the location of the selected area may be chosen based upon the location of any leakage current in the semiconductor device. A substantially significant electric field is an electric field (measured in $MV*cm^{-1}$ or million volts per centimeter) that would cause $H_2$ in an $SiO_2$ layer of a semiconductor device to react with the defects and irregularities in $SiO_2$. In certain semiconductor devices that have already experienced breakdown damage, it may be possible to detect the breakdown precursors without application of the significant electric field. Consequently, it may be desirable to test the semiconductor devices without applying the electric field.

In step 808, the spectroscopy of the one selected area of the thin dielectric layer is measured under the application of the substantially significant electric field. In step 810, it is then determined whether the measured spectroscopy exhibits—based on the criteria taught above—the presence of at least one breakdown precursor, i.e., $H_2$, H interstitial radical, H attached radical, and H attached dimer.

In step 812, the intensity of the substantially significant electric field optionally applied in step 806 may be increased. In such a case, the spectroscopy of the area may be measured again (step 814) and analyzed to determine whether this spectroscopy exhibits the presence of at least one breakdown precursor from the group consisting of $H_2$, H interstitial radical, H attached radical, and H attached dimer (step 816). In step 818, the electric field strength may be increased again to increase the potential for breakdown chemical reactions to occur in the thin dielectric layer. If such increased testing is desired, the method returns to step 812. If not, then the method is concluded. Such increased field strength may be desirable where a semiconductor device has not exhibited the potential for breakdown chemical reactions under the lower field strengths or alternatively to conduct accelerated testing of the device.

Measuring the spectroscopy of the selected area of the thin dielectric layer may be performed using various methods. Based on the foregoing equations, detecting and monitoring changes in $H_2$ such as those due to the creation of attached H states using Raman and infra-red spectroscopy to observe changes with and without electric field stress can be used during device fabrication to determine device quality and also to screen potentially bad devices. Electron-Spin Resonance (ESR) may also be used for ESR active configurations (eg., the attached H state) and x-ray absorption/scattering (XANES and XAFS) can detect local structural changes in the material.

Electron Spin Resonance Spectroscopy (ESR) may be used to detect H radicals; attached H; attached H dimer; and Si E and E'-centers. The Hydrogen radical is ESR active due to its single unpaired electron. ($H_2$ is not ESR active because its two electrons are paired in a spin singlet.) Thus, the cracking of $H_2$ into two H radicals can be observed by detecting the appearance and change in the H radical spin resonance intensity.

When the H radical attaches to an O (oxygen) in $SiO_2$, the unpaired electron remains unpaired, but goes into a different ESR active state. There is a detectable g-factor (resonance energy) difference between H radical and attached H to O. The decrease of one ESR signal along with the associated increase in the other signal can be used to determine the rate of attaching reactions or H separation reactions.

The attached H dimer state is spin singlet and is not ESR active. Thus, monitoring changes in the H interstitial radical, attached H radical ESR signals along with their intensity changes leads to information on the rate of formation of attached H dimer states. Detecting Si dangling bond ESR and its changes can be used to examine the formation of the above H states in the interface region where the strain energy from joining the oxide and semiconductor materials together makes the formation of the above H states more favorable.

Raman and infra-red (IR) spectroscopy may also be used to detect $H_2$; attached H radical and dimer; and Si—O bond vibrations. Changes in the Raman and IR signals for $H_2$ vibrational modes allows the observation of the amount of $H_2$ along with its cracking to form H radical. Attached H radical and dimer will have distinct detectable vibrational frequencies and intensities that can be monitored.

Optical absorption, reflection, and transmission may be used to detect the attached H radical and dimer states within the $SiO_2$ bandgap (approximately 9 eV). These states can be detected and monitored by optical absorption, reflection, and transmission arising from exciting a bound attached electron into the conduction band.

Finally, X-ray Absorption Near Edge Structure (XANES) and X-ray Absorption Fine Structure (XAFS) may be used to measure small structural changes arising from the formation of the above H attached and radical states. In this case, the O atom that H attaches to changes position by approximately 0.5 Angstroms.

Figure 9:
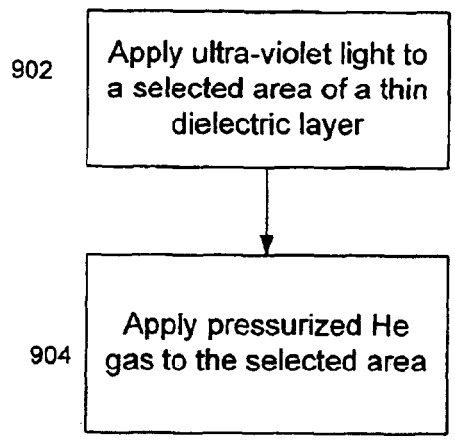
FIG. 9 of the drawings is a flow diagram of a first approach to reducing the dielectric breakdown in a semiconductor device having a thin dielectric layer.
Figure 10:
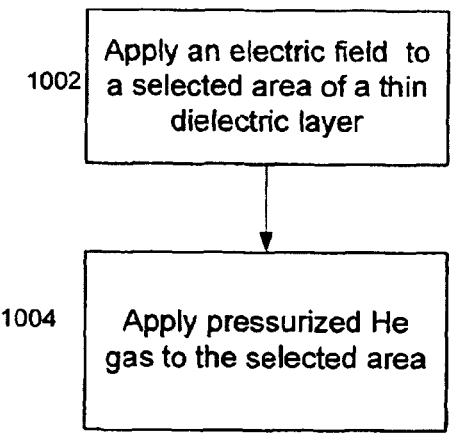
FIG. 10 of the drawings is a flow diagram of a second approach to reducing the dielectric breakdown in a semiconductor device having a thin dielectric layer.
Figure 11:
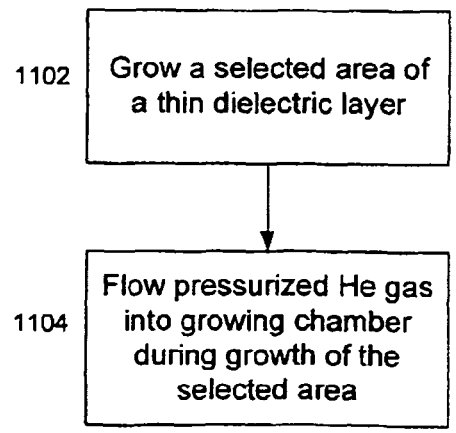
FIG. 11 of the drawings is a flow diagram of a third approach to reducing the dielectric breakdown in a semiconductor device having a thin dielectric layer.

FIG. 9-11 illustrate three potential embodiments for reducing the dielectric breakdown of a semiconductor device having a thin layer dielectric. In general, reducing the dielectric breakdown is accomplished by substituting $H_2$ molecules in the interstitial sites of the $SiO_2$ with elements or molecules that do not react with Si or O to form the undesired attached states as described above. For instance, in one embodiment, the $H_2$ may be reduced—in turn reducing dielectric breakdown—by pumping it off and replacing it with helium (He) or any other relatively inert gas that has molecular size approximating that of the H atom.

FIG. 9 illustrates a first method for reducing dielectric breakdown. Generally, H interstitial radicals can move easily form one $SiO_2$ interstitial void to another, while $H_2$ cannot. In step 902, ultraviolet (UV) light may be applied to a selected area of the thin dielectric layer (for example, oxide gate) in order to break the $H_2$ molecules into H interstitial radicals. In step 904, pressurized Helium gas may then be applied to the selected area to essentially push the H atoms out of the dielectric while the Helium atoms fill the interstitial region.

In a second embodiment illustrated in FIG. 10, a substantially significant electric field, rather than UV light, may be applied to the selected area in order to break the $H_2$ molecules into H interstitial radicals (step 1002). Once again, pressurized Helium gas may then be applied to the selected area to essentially push the H atoms out of the dielectric while the Helium atoms fill the interstitial region (step 1004). The applied electric field may also be a pulsed electric field. The length of each pulse may then be adjusted such that the attached radical state can be formed while driving the H interstitial radicals out of the oxide with the pressurized He.

In yet another embodiment illustrated in FIG. 11, the selected area may be grown using known techniques for growing semiconductor layers (step 1102). In step 1104, a pressurized Helium gas may then be flowed into the growing chamber in order to displace the $H_2$ molecules and replace them with He during the growth process.

While various embodiments of the application have been described, it will be apparent to those of ordinary skill in the art that many more embodiments and implementations are possible that are within the scope of this invention. Accordingly, the invention is not to be restricted except in light of the attached claims and their equivalents.

The invention claimed is:

1. A method of detecting the breakdown potential of a semiconductor device having a thin dielectric layer, the method comprising:
   measuring a first spectroscopy of at least one selected area of the thin dielectric layer;
   determining whether the first spectroscopy of the at least one selected area of the thin dielectric layer exhibits the presence of a breakdown precursor;
   applying a substantially significant applied electric field across the at least one selected area of the thin dielectric layer while measuring the first spectroscopy of the at least one selected area of the thin dielectric layer; and
   determining whether the first spectroscopy of the at least one selected area of the thin dielectric layer exhibits a decrease in the presence of the breakdown precursor $H_2$ in response to applying the substantially significant applied electric field.

2. The method according to claim 1 further comprising:
measuring a second spectroscopy of at least one selected area of the thin dielectric layer; and
determining whether the second spectroscopy of the at least one selected area of the thin dielectric layer exhibits the presence of at least one breakdown precursor from the group consisting of H interstitial radical, H attached radical, and H attached dimer.

3. The method according to claim 2 further comprising:
applying the substantially significant applied electric field across the at least one selected area of the thin dielectric layer while measuring the second spectroscopy of the at least one selected area of the thin dielectric layer; and
determining whether the second spectroscopy of the at least one selected area of the thin dielectric layer under the influence of the applied electric field exhibits an increase in the presence of at least one breakdown precursor from the group consisting of H interstitial radical, H attached radical, and H attached dimer.

4. The method according to claim 2 further comprising:
repetitively increasing the substantially significant applied electric field across the at least one selected area of the thin dielectric layer by the predetermined amount after measuring the first spectroscopy and the second spectroscopy of the at least one selected area of the thin dielectric layer; and
for each repetitive increase of the substantially significant applied electric field, determining whether the first spectroscopy and the second spectroscopy of the at least one selected area of the thin dielectric layer under the influence of the increased applied electric field exhibits a change in the amount of at least one breakdown precursor from the group consisting of $H_2$, H interstitial radical, H attached radical, and H attached dimer.

5. The method according to claim 2 further comprising selecting the at least one selected area of the thin dielectric layer for measurement based upon the location of a leakage current in the semiconductor device.

6. The method according to claim 2 wherein measuring the second spectroscopy includes the step of using Electron Spin Resonance Spectroscopy to measure the physical characteristics caused by the at least one selected from the group consisting primarily of Hydrogen ESR, Attached H ESR, Attached H dimer ESR and Si E and E'-center ESR.

7. The method of claim 2 wherein measuring the first spectroscopy or the second spectroscopy further includes the step of using infra-red spectroscopy to measure the physical characteristics caused by the at least one selected from the group consisting of $H_2$, attached H radical and dimer, and Si—O bond vibrations.

8. The method according to claim 7 wherein the infra-red spectroscopy is performed with a Raman Spectroscope.

9. The method according to claim 2 wherein measuring the second spectroscopy includes the step of using Glancing Incidence X-Ray Reflection/Refraction (GIXR) to measure the physical characteristics caused by small spatial density changes in an interface (Metal/SiO2) region caused by the formation of the above H attached and radical states.

10. The method according to claim 2 wherein measuring the second spectroscopy includes the step of using optical absorption, reflection, and transmission to measure the physical characteristics caused by the group consisting of attached H radical and dimer states.

11. The method according to claim 2 wherein measuring the second spectroscopy includes the step of using X-ray Absorption Near Edge Structure (XANES) to measure small structural changes arising from the formation of the above H attached and radical states.

12. The method according to claim 2 wherein measuring the second spectroscopy includes the step of using X-ray Absorption Fine Structure (XAFS) to measure small structural changes arising from the formation of the above H attached and radical states.

13. The method of claim 2, wherein the first spectroscopy and second spectroscopy are identical.

14. The method of claim 2, wherein the first spectroscopy and second spectroscopy are different.

15. A method of detecting the breakdown potential of a semiconductor device having a thin dielectric layer, the method comprising:
measuring a spectroscopy of at least one selected area of the thin dielectric layer;
determining whether the spectroscopy of the at least one selected area of the thin dielectric layer exhibits the presence of at least one breakdown precursor from the group consisting of H interstitial radical, attached radical, and H attached dimer;
applying a substantially significant applied electric field across the at least one selected area of the thin dielectric layer while measuring the spectroscopy of the at least one selected area of the thin dielectric layer; and
determining whether the spectroscopy of the at least one selected area of the thin dielectric layer exhibits an increase in the presence of at least one breakdown precursor selected from the group consisting of H interstitial radical, H attached radical, and H attached dimer in response to applying the substantially significant applied electric field.

16. The method according to claim 15 wherein measuring the spectroscopy includes the step of using Electron Spin Resonance Spectroscopy to measure the physical characteristics caused by the at least one selected from the group consisting primarily of Hydrogen ESR, Attached H ESR, Attached H dimer ESR and Si E and E'-center ESR.

17. The method according to claim 15 wherein measuring the spectroscopy includes the step of using Glancing Incidence X-Ray Reflection/Refraction (GIXR) to measure the physical characteristics caused by small spatial density changes in an interface (Metal/SiO2) region caused by the formation of the above H attached and radical states.

18. The method of claim 15, further comprising:
determining whether the spectroscopy of the at least one selected area of the thin dielectric layer exhibits the presence of the breakdown precursor $H_2$; and
determining whether the spectroscopy of the at least one selected area of the thin dielectric layer exhibits a decrease in the presence of the breakdown precursor $H_2$ in response to applying the substantially significant applied electric field.

19. A method of detecting the breakdown potential of a semiconductor device having a thin dielectric layer, the method comprising:
measuring a spectroscopy of at least one selected area of the thin dielectric layer;
determining whether the spectroscopy of the at least one selected area of the thin dielectric layer detects the presence of at least one breakdown precursor;
applying a substantially significant applied electric field across the at least one selected area of the thin dielectric layer while measuring the spectroscopy of the at least one selected area of the thin dielectric layer; and determining whether the spectroscopy of the at least one selected area of the thin dielectric layer detects a change in the amount of the at least one breakdown precursor in response to applying the substantially significant applied electric field, wherein the at least one breakdown precursor is selected from the group consisting of $H_2$, H interstitial radical, H attached radical, and H attached dimer, and wherein said change in amount of at least one breakdown precursor indicates the breakdown potential of a semiconductor device having a thin dielectric layer.

20. The method of claim 19, wherein the spectroscopy further comprises a first spectroscopy and a second spectroscopy.

21. The method of claim 20, wherein the first spectroscopy detects the presence and the change in amount of the at least one breakdown precursor comprising $H_2$ and wherein the second spectroscopy detects the presence and the change in amount of the at least one breakdown precursor selected from the group consisting of H interstitial radical, H attached radical, and H attached dimer.

22. The method of claim 20, wherein the first spectroscopy and the second spectroscopy are identical.

23. The method of claim 20, wherein the first spectroscopy and the second spectroscopy are different.

24. The method of claim 20, wherein the first spectroscopy comprises at least one member selected from the group consisting of Raman spectroscopy and infra-red spectroscopy.

25. The method of claim 20, wherein the second spectroscopy comprises at least one member selected from the group consisting of Raman spectroscopy, infra-red spectroscopy, electron spin resonance spectroscopy, and X-ray absorption spectroscopy.

* * * * *

UNITED STATES PATENT AND TRADEMARK OFFICE
CERTIFICATE OF CORRECTION

PATENT NO. : 7,943,401 B2
APPLICATION NO. : 12/114587
DATED : May 17, 2011
INVENTOR(S) : Jamil Tahir-Kheli et al.

It is certified that error appears in the above-identified patent and that said Letters Patent is hereby corrected as shown below:

On the Title page of the Patent, Item (12) and Item (75) Inventors:, "Jamil Tamir-Kheli" should be --Jamil Tahir-Kheli--.

Signed and Sealed this
Sixteenth Day of August, 2011

David J. Kappos
*Director of the United States Patent and Trademark Office*